(12) United States Patent
Hauck et al.

(10) Patent No.: US 6,926,715 B1
(45) Date of Patent: *Aug. 9, 2005

(54) CARDIAC VALVE LEAFLET ATTACHMENT DEVICE AND METHODS THEREOF

(76) Inventors: Wallace Neil Hauck, 21 Shearwater, Irvine, CA (US) 92604; Samuel Victor Lichtenstein, 6410 Cedarhurst St., Vancouver (CA), V6N 1T1; Hosheng Tu, 15 Riez, Newport Beach, CA (US) 92657

(*) Notice: Subject to any disclaimer, the term of this patent is extended or adjusted under 35 U.S.C. 154(b) by 0 days.

This patent is subject to a terminal disclaimer.

(21) Appl. No.: 10/457,757

(22) Filed: Jun. 9, 2003

Related U.S. Application Data

(63) Continuation-in-part of application No. 10/000,992, filed on Nov. 15, 2001, now Pat. No. 6,575,971.

(51) Int. Cl.[7] .............................................. A61B 18/12
(52) U.S. Cl. ........................................ 606/41; 606/49
(58) Field of Search ............................ 606/41, 45, 47, 606/49–52, 205

(56) References Cited

U.S. PATENT DOCUMENTS

| | | |
|---|---|---|
| 5,314,424 A | 5/1994 | Nicholas |
| 5,403,312 A | 4/1995 | Yates et al. |
| 5,456,684 A | 10/1995 | Schmidt et al. |
| 5,527,313 A | 6/1996 | Scott et al. |
| 5,582,611 A | 12/1996 | Tsuruta et al. |
| 5,609,598 A | 3/1997 | Laufer et al. |
| 5,891,160 A | 4/1999 | Williamson, IV et al. |
| 5,928,224 A | 7/1999 | Laufer |
| 6,068,628 A | 5/2000 | Fanton et al. |
| 6,068,629 A | 5/2000 | Haissaguerre et al. |
| 6,126,658 A | 10/2000 | Baker |
| 6,162,233 A | 12/2000 | Williamson, IV et al. |
| 6,165,183 A | 12/2000 | Kuehn et al. |
| 6,187,003 B1 | 2/2001 | Buysse et al. |
| 6,203,553 B1 | 3/2001 | Robertson et al. |
| 6,267,781 B1 | 7/2001 | Tu |
| 6,269,819 B1 | 8/2001 | Oz et al. |
| 6,283,962 B1 | 9/2001 | Tu et al. |
| 6,306,133 B1 | 10/2001 | Tu et al. |
| 6,322,559 B1 | 11/2001 | Daulton et al. |
| 6,485,489 B2 | 11/2002 | Teirstein et al. |
| 6,575,971 B2 * | 6/2003 | Hauck et al. .................. 606/52 |

* cited by examiner

*Primary Examiner*—Roy D. Gibson
*Assistant Examiner*—Aaron Roane

(57) ABSTRACT

A medical device system comprising a guide catheter and a leaflet fastening applicator, the guide catheter having suitable dimensions for deployment and insertion percutaneously into a human heart in a vicinity of a heart valve, the leaflet fastening applicator having a size allowing insertion through the guide catheter and being capable of holding portions of opposing heart valve leaflets, wherein the fastening applicator comprises a pair of grasping-electrodes adapted for holding and engaging the portions of opposing heart valve leaflets together and for applying energy to fasten the portions, in which valve leaflets can be captured and securely fastened, thereby improving coaptation of the leaflets and improving competence of the valve.

8 Claims, 16 Drawing Sheets

CARDIAC VALVE LEAFLET ATTACHMENT DEVICE AND METHODS THEREOF

CROSS-REFERENCE TO RELATED APPLICATIONS

This patent application is a continuation-in-part application of application Ser. No. 10/000,992 filed Nov. 15, 2001, entitled "Cardiac Valve Leaflet Stapler Device and Methods Thereof", now U.S. Pat. No. 6,575,971.

FIELD OF THE INVENTION

The present invention generally relates to new coupling devices and methods for use. More particularly, this invention relates to a percutaneous device, which grasps, secures, and then attaches two adjacent heart valve leaflets with staples or an RF coupling element causing a shortening of the leaflet in the desired direction or orientation. The invention also relates to a method for treating a valvular annulus comprising steps of fastening portions of two opposite leaflets and applying energy to the valvular annulus adapted for shrinking at least a portion of the annulus tissue.

BACKGROUND OF THE INVENTION

The heart is a four-chambered organ located in the thoracic space. The heart is responsible for pumping blood through the body, through two distinct circuits. One circuit takes blood low in oxygen from the systemic venous system, which collects in the right atrium (one chamber). The atrium pumps the blood into the immediately lower chamber, the right ventricle. In passing from the atrial chamber to the ventricular chamber, the blood passes through the "tricuspid" valve opening, so named because of the three leaflets (cusps) of the valve. The right ventricle contracts to pump the blood into the lungs (second circuit) and in so contracting, forces the tricuspid valve leaflets closed, thus preventing backflow of blood into the right atrium.

The oxygenated blood flowing back to the heart from the lungs enters the left atrium (third chamber) and collects there until the atrium contracts and pumps the blood through the mitral valve into the immediately lower chamber, the left ventricle, during diastole. When the left ventricle contracts to pump the blood into the systemic circulation (back to the first circuit) during systole, the mitral valve leaflets are closed, preventing backflow of blood into the left atrium and the pulmonary circulation. The mitral valve is comprised of two valve leaflets. The atria contract simultaneously, as do the ventricles.

Another set of valves is present in the main artery of the left ventricle, the aorta and the main artery of the right ventricle, the pulmonary artery. These valves are called the aortic and pulmonary valves, respectively and they are similar in appearance.

The anatomy of the mitral and tricuspid valves is similar, but quite distinctly different from the anatomy of the aortic and pulmonary valves. These valves are comprised of the following six different components: the left (or right) atrial wall, the left (or right) ventricular wall, the annulus, the leaflets, the chordae tendinae and the papillary muscles. The annulus is a zone of junction that serves as the attachment of the muscular fibers of the atrium and the ventricle and as the attachment of the mitral (or tricuspid) valve. Annular tissue is pliable permitting contraction of the annular ring when the ventricles contract and thus narrowing the aperture.

The annulus forms the foundation for the leaflets, which are secured to the ventricular wall by way of the chordae tendinae, thin fibrous cords attaching the free edges of the leaflets to the papillary muscles, which are elevations or extensions of the ventricular wall. All structures are covered by endothelial cell lining but the contractile elements (muscles) of the atria and ventricles are capable of independent movement. The other structures are largely fibrous in nature, composed of dense fibrous connective tissue and collagen.

When the ventricles contract during systole, the pressure within the ventricles forces the leaflets upward until the free edges contact. This is called coaptation. The free edges of the leaflets are inhibited by the chordae tendinae from prolapsing beyond the plane of the annulus and into the atrial chambers. When the normal mitral or tricuspid valves close, the valve becomes competent and no blood escapes through the annulus. The operation of these valves (plus the normal closure of the aortic and pulmonary valves) ensures that the heart functions as a one-way pump.

As one understands the complex operation of the mitral or tricuspid valves, one can begin to appreciate the number of possible causes for failure of proper function of these valves. Some of these are: loss of pliability of the annulus leading to decreased contractibility; widening of the annulus; thickening, shortening or swelling of the leaflets; dilation of the ventricle; elongation or breaking of the chordae tendinae; and elongation of the attachment of the chordae tendinae with the papillary muscles or ventricular wall.

Individual or combinations of these causes for failure eventually lead to loss of coaptation of the leaflets, loss of competence of the valve and decreased efficiency of the heart as a one-way pumping mechanism. When the latter occurs, various symptoms are seen in the patients, including breathlessness or lack of stamina and heart murmurs.

Repair of the incompetent valves is designed to address two functional conditions of the leaflets, either the opening or closing of the leaflets is increased or restricted. The former condition, called leaflet prolapse, exists when the free edge of one leaflet overrides the annulus when the ventricles contract. The latter condition occurs when the restricted leaflet motion prevents the leaflets from opening. The other possible functional condition is where the valve leaflets may be functionally normal, but the annulus does not contract or is too enlarged. When this occurs the leaflets will not close effectively.

The current accepted modes of treatment of these conditions described for the mitral and tricuspid valves include the following: valvuloplasty, in which the affected leaflets are remodeled to perform normally; repair of the chordae tendinae and/or papillary muscle attachments; and surgical insertion of an "annuloplasty" ring. This requires suturing a flexible support ring over the annulus and tucking the annulus to constrict the radial dimension.

Each of these procedures requires open-heart surgery and cardiopulmonary bypass procedure, in which the heart is removed from the blood circuits as the circuits have been described above and a pumping system circulates the blood through the patient during the surgical procedure. The heartbeat is stopped and the heart is usually cooled and infused with a cold nutrient solution during the procedure. Open-heart surgery with cardiopulmonary bypass is a very expensive procedure, requiring considerable time, multiple surgeons and a host of assisting personnel to operate the equipment, monitor the patient and proceed with caution but quickly for the patient's benefit. These procedures are also associated with serious risks, including death and adverse events for the patient and the patient has a long painful course of recovery, first in the hospital, then at home.

Oz et al. in U.S. Pat. No. 6,269,819 discloses an apparatus for repairing valve leaflets comprising a grasper capable of grabbing and co-apting the leaflets of valve to cure mitral regurgitation. The principles of the "grasper" arrangement and its mechanism as disclosed are incorporated herein by reference. Oz et al. does not disclose a medical system having a fastening applicator that comprises a pair of grasping-electrodes means adapted for holding and engaging portions of opposing heart valve leaflets together and for applying suitable energy to fasten the portions.

Robertson et al. in U.S. Pat. No. 6,203,553 discloses a surgical stapler for securing a prosthetic heart valve within a patient by driving a first leg of the stapler assembly through a peripheral cuff of the prosthetic heart valve and crimping a second leg of the stapler assembly in a direction toward the first leg such that the second leg pierces a portion of heart tissue surrounding the prosthetic valve for securing purposes. The principles of "stapler" arrangement and its securing mechanism as disclosed are incorporated herein by reference. Robertson et al. does not disclose a medical system having a fastening applicator that comprises a pair of grasping-electrodes means adapted for holding and engaging portions of opposing heart valve leaflets together and for applying suitable energy to fasten the portions.

This invention discloses a series of devices to be used to repair leaking valves with normal leaflets (that is, abnormal annulus) or leaflet prolapse, without the disadvantages associated with open-heart surgery, because the device is inserted into the heart via the blood vessels, through the skin in the groin or neck area percutaneously. During the procedure, the patient may be awake, sedated or anesthetized and the device and progress of the procedures are monitored and guided using fluoroscopy and echocardiography, both noninvasive methods, in the continuously beating heart. Obviously fewer personnel are required to assist with the procedure. When the procedure is completed the patient may be discharged within hours to days. All of these contrasting features to open-heart procedures make the use of the stapling device a potentially valuable resource for the interventional cardiologist. These specialists will be able to add yet another "minimally invasive" procedure for treatment of their patients.

SUMMARY OF THE INVENTION

In general, it is an object of the present invention to provide a method and an improved medical device for attaching adjacent leaflet edges or foreshortening individual leaflets. The leaflets referred to herein include mitral and tricuspid leaflets, and may also include aortic and pulmonary valve leaflets, venous valve leaflets, defects within the heart in the atria or ventricles and any other intravascular structure (s) which may need to be stapled together or foreshortened as described for the mitral and tricuspid valves.

It is another object of the present invention to provide a method and device for approaching the desired location on a leaflet and attaching the device to the desired location on the leaflet through various means, including suction or metallic hooks. For example, using suction, the end of the leaflet holder device is placed upon the leaflet and a negative pressure (suction) is applied wherein the leaflet tissue is sucked for a short distance into the end of the leaflet holder device.

It is another object of the present invention to provide a method and device for approaching an adjacent leaflet edge and securing the leaflet by one of various means, such that when the two leaflet holding devices containing the secured leaflets are withdrawn into the distal end of the tubular gripper, the two leaflet edges are in close apposition, possibly touching each other. The device system may apply suction to grip at least two of the heart valve leaflets to enter the lumen of the tubular gripper adapted for fastening the portions of opposing heart valve leaflets together.

It is still another object of the present invention to provide a method and device for attaching two leaflets or for foreshortening one leaflet by insertion of a metal or plastic staple, which when crimped physically or electronically, permanently attaches the staple to the one or two leaflets. The configuration of the staple may be linear, curved, kinked, spiral or any other configuration that would permanently secure the leaflet(s).

It is further another object of the present invention to provide a method and device for transporting the staple to the desired site of attachment, in the proper position to accomplish the attachment, without the possibility of releasing the free staple into the heart chamber. Following the attachment the staple must be released from its holder and then the secured leaflet(s) will then be released from the leaflet holding device(s). The method and device of securing the staple prior to its insertion into the leaflet(s) may be through use of a breakable fiber or a metallic link. For example, the metallic link may be one that is broken at a specified temperature. When electrical energy, such as radiofrequency voltage is applied to the metallic line, the temperature rises to a level wherein the link is broken and the previously attached staple becomes free from its metallic line tether.

In one preferred embodiment, it is provided a device system for treating a valvular annulus comprising a guide catheter and a leaflet fastening applicator, the guide catheter having suitable dimensions for deployment and insertion into a human heart in a vicinity of a heart valve and comprising a non-ablative energy means for shrinking at least a portion of the valvular annulus, the leaflet fastening applicator having a size allowing insertion through the guide catheter and being capable of holding portions of opposing heart valve leaflets, wherein the fastening applicator comprises a pair of grasping-electrodes adapted for holding and engaging the portions of opposing heart valve leaflets together and for applying radiofrequency energy to fasten the portions, wherein a first of the grasping-electrodes comprises a plurality of spikes and a second of the grasping-electrodes comprises a plurality of recesses configured to receivably match and engage the spikes of the first grasping-electrode, wherein the catheter comprises at least a gripper inside the catheter, the gripper having a suitable opening sized and configured for applying vacuum suction to releasably grip one of the heart valve leaflets.

Further, a method for fastening portions of opposing heart valve leaflets in a patient, the method comprising means for holding the portions of opposing heart valve leaflets close to each other and applying energy to jointly fasten the portions together. Some aspects of the invention relate to a method for fastening a portion of a first valve leaflet with a portion of a second valve leaflet in a patient, comprising steps of holding the portion of the first valve leaflet in contact with the portion of the second valve leaflet and applying a plurality of energy sources to securely fasten the two portions together, wherein the plurality of energy sources is selected from a group consisting of radiofrequency energy, ultrasound energy, laser energy, microwave energy, and electromagnetic energy.

It is another preferred object to provide a method for fastening a first edge of a first valve leaflet to a second edge of an opposite second valve leaflet in a patient, the method comprising: first, introducing a medical device into a vicinity of a valve needed for repairing, the medical device comprising a catheter and a leaflet fastening applicator, the catheter having suitable dimensions for deployment and insertion into the patient in the vicinity of the valve, the leaflet fastening applicator having a size allowing insertion through the catheter and being capable of holding the first edge of the first valve leaflet to the second edge of the opposite second valve leaflet, wherein the fastening applicator comprises a pair of fastening elements adapted for holding and engaging the first edge and second edge of valve leaflets close to each other; and applying energy to the fastening elements to securely fasten the first edge of the first valve leaflet to the second edge of the second valve leaflet.

Briefly, access to the blood vascular system is obtained through a skin puncture over a peripheral vein or artery. An introducer device is used to secure the vascular access and a guidewire is passed down the introducer into the vessel and advanced into the heart. A guide catheter is placed over the guidewire and advanced over the guidewire to the desired position in the heart. The guidewire is withdrawn from the guide catheter and the leaflet holder device is inserted and advanced into the guide catheter to the desired location in the heart. The leaflet holder device is then manipulated into position and the leaflet(s) is/are secured and the tips of the leaflet holder device are withdrawn slightly into the end of the guide catheter. When the interventional cardiologist is confident that the proper position on the leaflet(s) is secured, the staple(s) located in the end of the guide catheter is/are attached to the leaflet(s). The staple is then released from the guide catheter attachment via breakable fiber or breakable metallic link. Finally, the leaflet(s) is/are released from the leaflet holding device and the leaflet(s) is/are free to function with the restrictions imposed by the staple. Multiple sites may be stapled in the same procedure.

In one embodiment, the leaflet holding device consists of a tube used to attach and secure one leaflet. Use of two such leaflet holder devices enables the user to grasp and secure two leaflets. In the embodiment, the guide catheter, a separate tube-shaped device, contains the staples and the staple securing system.

In another embodiment, the leaflet holder device and the guide catheter/staple holding device are one and the same device. In this device, the staple holding device may be stationary or may be moveable for some part of the length of the guide catheter.

Some aspects of the invention relate to a method for treating a valvular annulus, comprising: fastening portions of two opposite leaflets; and applying energy to the valvular annulus adapted for shrinking at least a portion of the annulus tissue. In one embodiment, the steps of fastening portions of two opposite leaflets and applying energy are carried out percutaneously. In another embodiment, it is provided a method for fastening a portion of a first valve leaflet with a portion of a second valve leaflet in a patient, comprising steps of holding the portion of the first valve leaflet in contact with the portion of the second valve leaflet and applying a plurality of energy sources to securely fasten the two portions together.

BRIEF DESCRIPTION OF THE DRAWINGS

Additional objects and features of the present invention will become more apparent and the invention itself will be best understood from the following Detailed Description of the Exemplary Embodiments, when read with reference to the accompanying drawings.

DETAILED DESCRIPTION OF THE EXEMPLARY EMBODIMENTS

Referring to FIG. 1 through FIG. 16, what is shown is various views of the heart structures discussed and one embodiment of the present invention.

Figure 1:
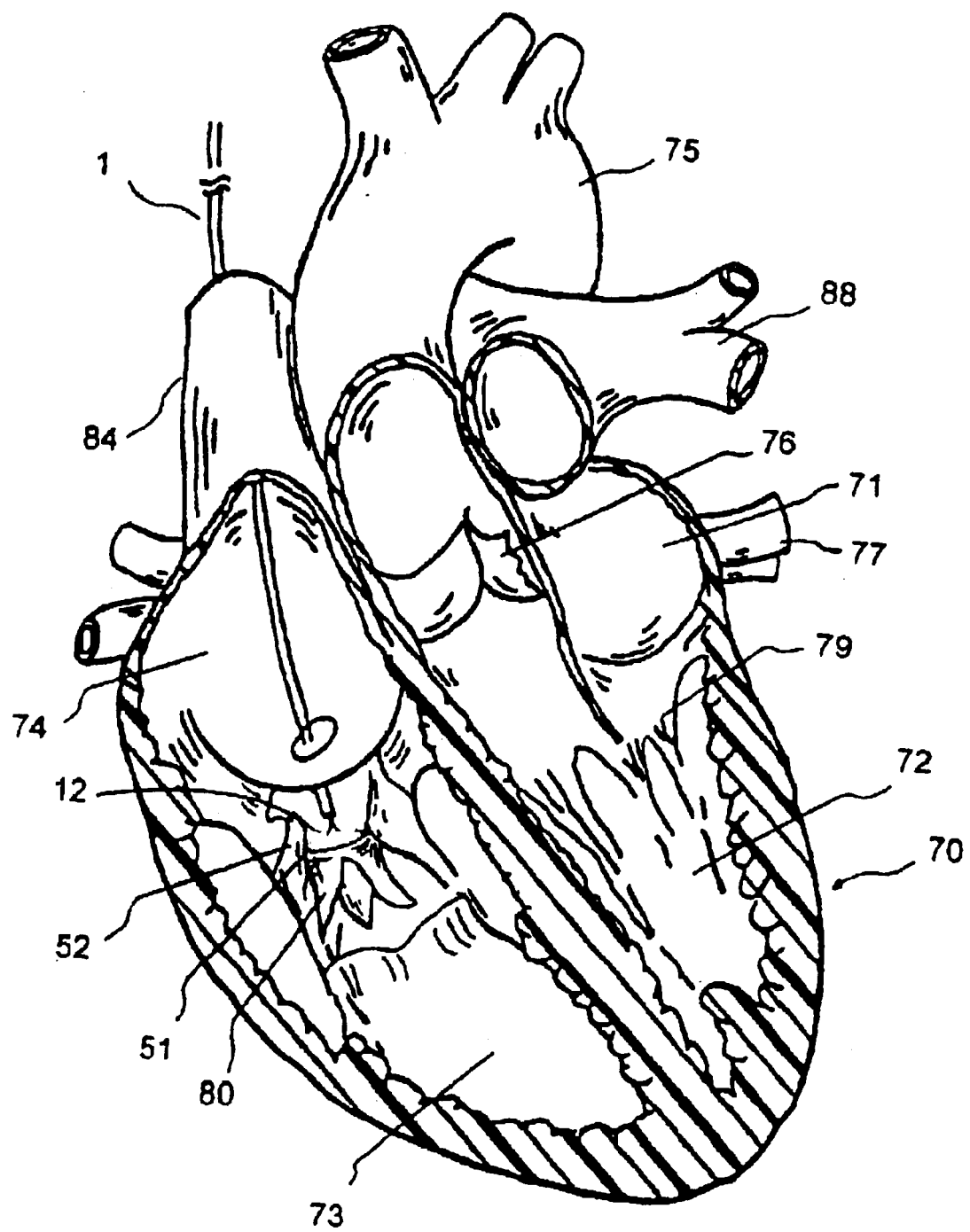
FIG. 1 is a cutaway schematic of the heart showing the chambers and the spatial relationships of the various anatomical features discussed in the invention.

FIG. 1 shows a cut away schematic of the heart depicting the right atrium 74, left atrium 71, right ventricle 73, and left ventricle 72. The aorta 75 of the heart 70 connects with the left ventricle 72 and contains an aortic valve 76. Pulmonary artery 77 connects with the right ventricle 73 through a pulmonary valve. Left atrium 71 communicates with the left ventricle 72 through a mitral valve 79. The right atrium 74 communicates with the right ventricle 73 through a tricuspid valve. Oxygenated blood is returned to the heat 70 via pulmonary veins 88. In a perspective illustration, a device or catheter is inserted into the right atrium 74 and is positioned through the inner wall 51 and the annular structure 52 of the tricuspid valve leaflets 80. The leaflets 80 of the tricuspid valve open toward the ventricle side. Blood returned from the superior vena cava 84 and the inferior vena cava flows into the right atrium 74. Subsequently, blood flows from the right atrium 74 to the right ventricle 73 through the tricuspid valve. Therefore, the grasping-electrodes 12 of the catheter shaft 1 does not interfere with the leaflet movement during the proposed less invasive thermal fastening for the leaflets of the invention. The term "grasping-electrode" is meant to indicate herein an electrode having means for grasping/fastening an object and providing energy for intended use.

Figure 2:
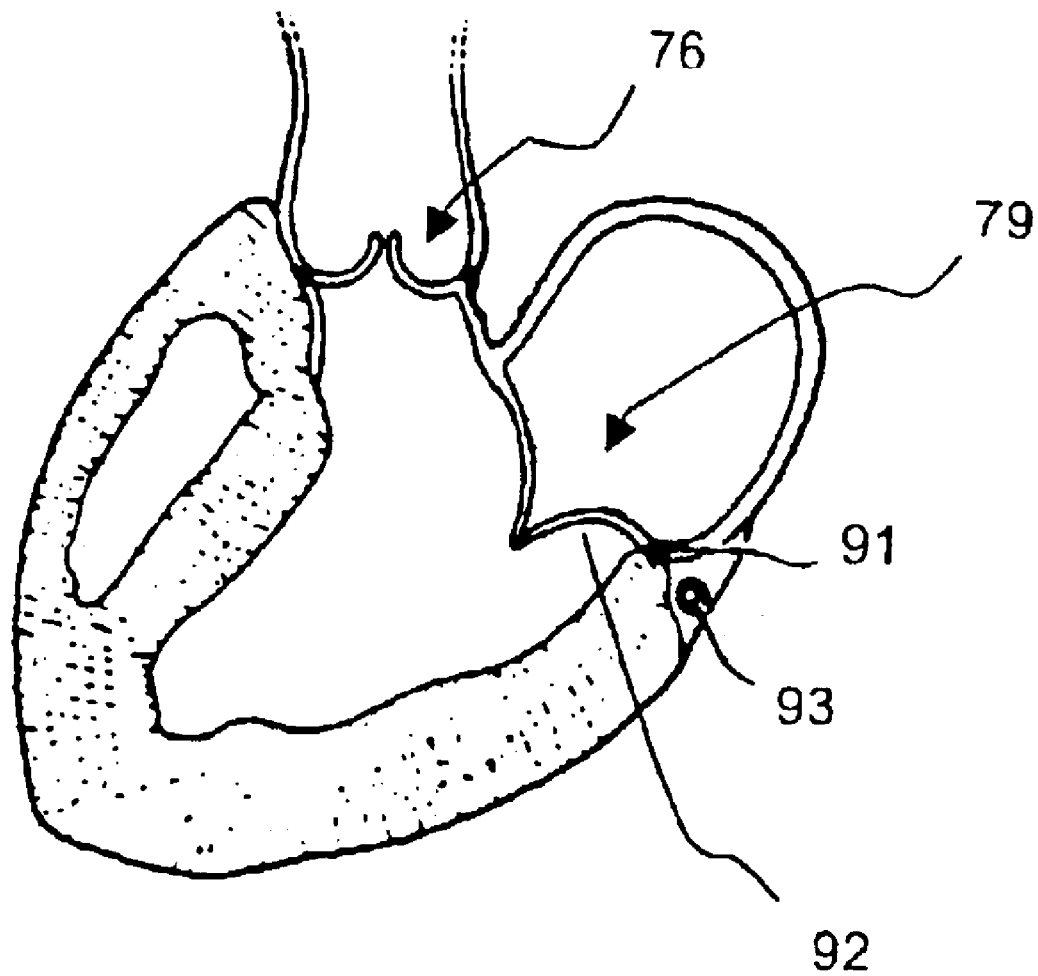
FIG. 2 is a cutaway schematic of the heart showing the relationships of the annulus to the leaflets and the relationship of the mitral valve to the aortic valve.

FIG. 2 shows a cutaway diagram of part of the heart, containing the mitral valve 79 and aortic valve 76 and showing the relationships between the annulus 91 and the leaflets 92 of the mitral valve 79. The circumflex artery 93 is located adjacent the mitral annulus 91.

Figure 3:
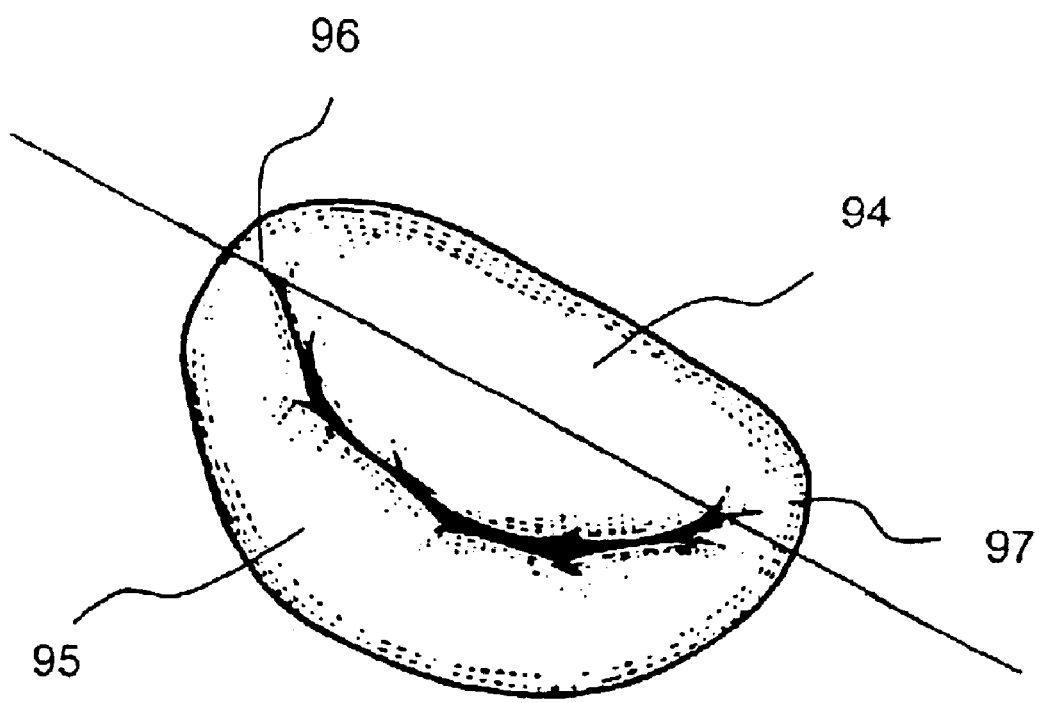
FIG. 3 is a top-down view of the mitral valve showing the annulus and the two leaflet tops.

FIG. 3 shows a top-down view of the mitral valve 91, looking through the left atrium 71. The relative positions of the anterior valve leaflet 94 and posterior valve leaflet 95 are shown, as are the antero-lateral commissure 96 and postero-medial commissure 97.

Figure 4:
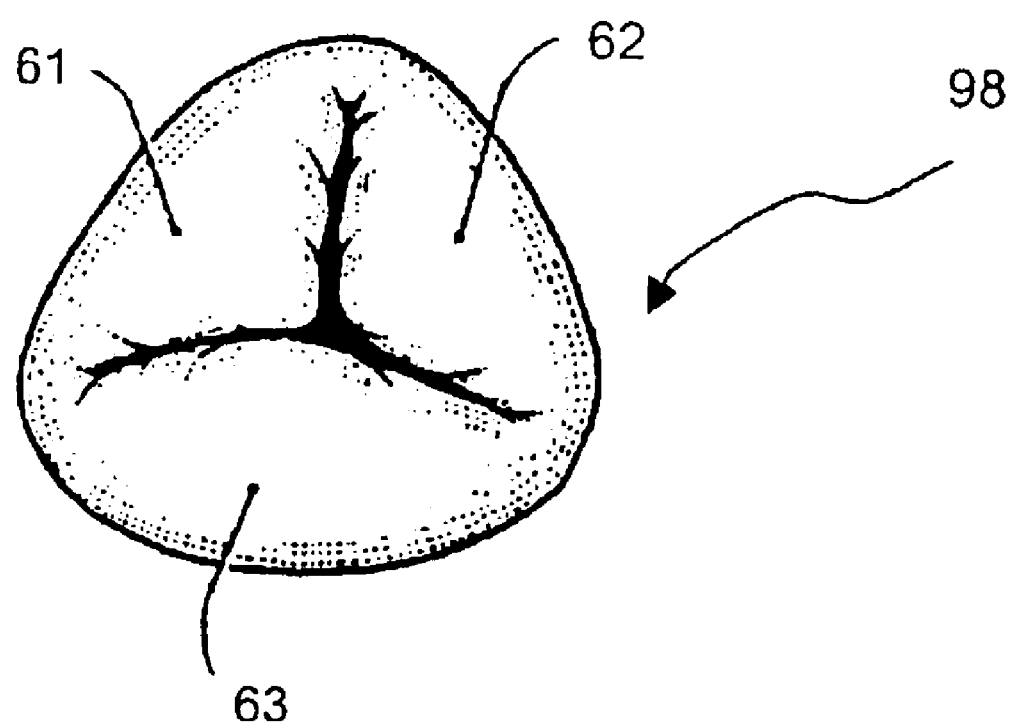
FIG. 4 is a top-down view of the tricuspid valve showing the annulus and the three leaflet tops.
Figure 5:
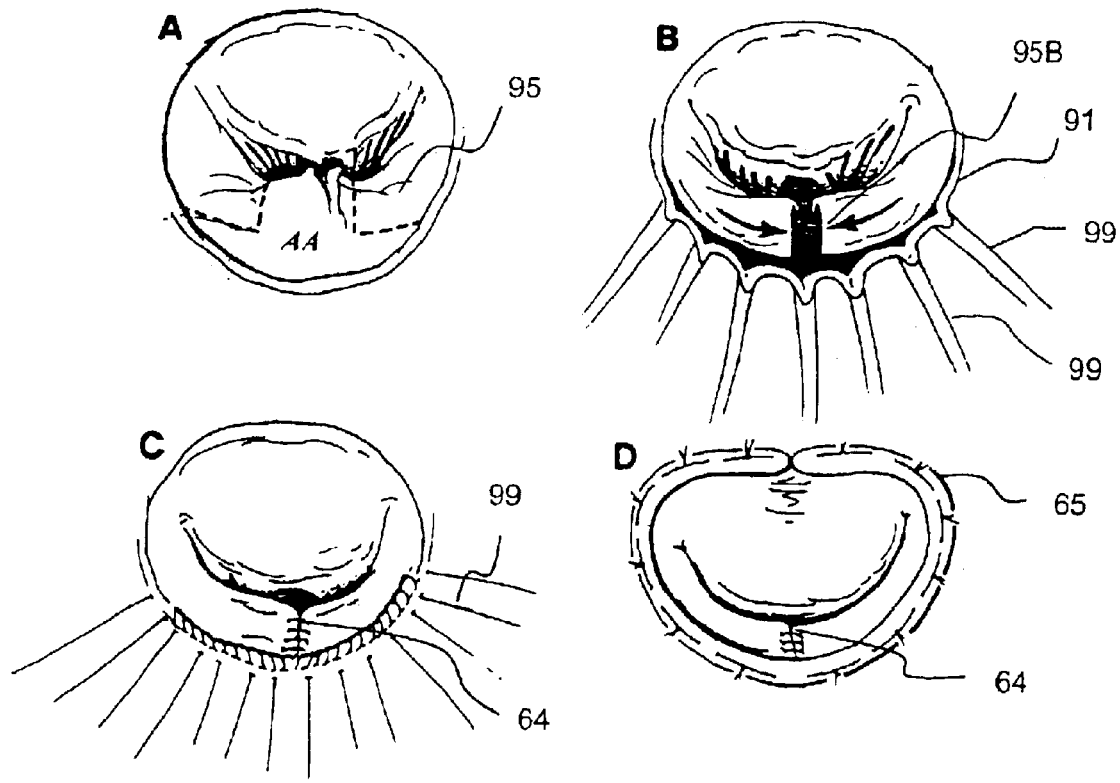
FIGS. 5A-5D is a four-part schematic drawing showing the steps in performing annuloplasty of the posterior leaflet and attaching an annuloplasty ring to the valve (prior art).

FIG. 4 shows a top-down view of the tricuspid valve 98, looking through the right atrium 74. The anterior valve leaflet 61, posterior valve leaflet 62 and septal valve leaflet 63 are shown, as are the three associated commissures.

For illustration purposes, FIGS. 5A-5D shows a top-down view of a mitral valve 79 in various stages of repair, according to the current practices of open-heart surgery under cardiopulmonary bypass (prior art). View FIG. 5A shows the area AA of the posterior leaflet 95 to be resected in the valvuloplasty. View FIG. 5B shows the resected posterior leaflet 95B and placement of stay-sutures 99 in the annulus 91, drawing and tightening the annulus. View FIG. 5C shows the closed valvuloplasty and the tightening of the annulus 91 along a suture line 64 above the posterior leaflet. View FIG. 5D shows the placement of an annuloplasty ring 65, which secures the mitral valve annulus 91 in the desired shape and size. Note the difference between the shape and size achieved by the surgery in view FIG. 5D, compared to that in view FIG. 5A.

Williamson, IV et al. in U.S. Pat. Nos. 5,891,160 and 6,162,233 discloses wire fasteners having legs and lengths for use in minimally invasive surgery, entire contents of which are incorporated herein by reference. More particularly, it is disclosed that the fasteners are manipulated into position and then immobilized by the legs thereof for tensioning, cutting and forming in situ so as to secure the prosthesis to the patient. However, Williamson, IV et al. does not disclose a medical system having a fastening applicator that comprises a pair of grasping-electrodes means adapted for holding and engaging portions of opposing heart valve leaflets together and for applying suitable energy to fasten the portions.

Kuehn et al. in U.S. Pat. No. 6,165,183 discloses a method for performing an edge-to-edge fastening/securing of opposing heart valve leaflets through a catheter percutaneously. The catheter includes a leaflet fastener applicator with a gripper to hold the heart valve leaflets while they are fastened. The principles of "gripping/securing/fastening" arrangement and the mechanism as disclosed are incorporated herein by reference. However, Kuehn et al. does not disclose a medical system having a fastening applicator that comprises a pair of grasping-electrodes means adapted for holding and engaging portions of opposing heart valve leaflets together and for applying suitable energy to fasten the portions.

Figure 6:
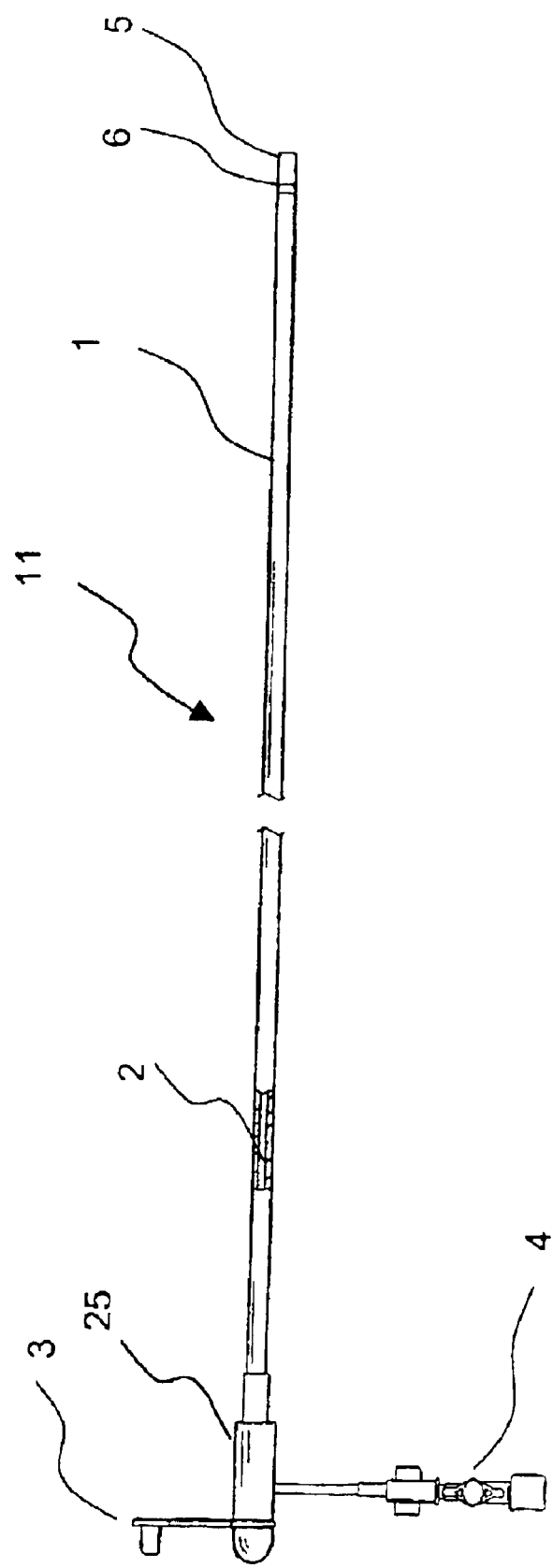
FIG. 6 is a schematic diagram of a guide catheter of the medical device according to the principles of the present invention.

FIG. 6 shows a schematic of a guide catheter 11 comprising a catheter sheath 1 and at least a lumen 2. The catheter 11 further comprises a cap 3 on the handle 25 of the guide catheter 11 for closing the lumen 2 of the catheter during placement, a sideport 4 for injection of solutions into the catheter (e.g., radiographic contrast medium), a radiopaque band 6 at about the distal end 5 to locate the end during placement on fluoroscopy. The solution for injection through the sideport 4 or the lumen 2 may be selected from a group consisting of heparin, aspirin, saline, antibiotic solution, anti-inflammatory solution, anti-septic solution or the like.

Figure 7:
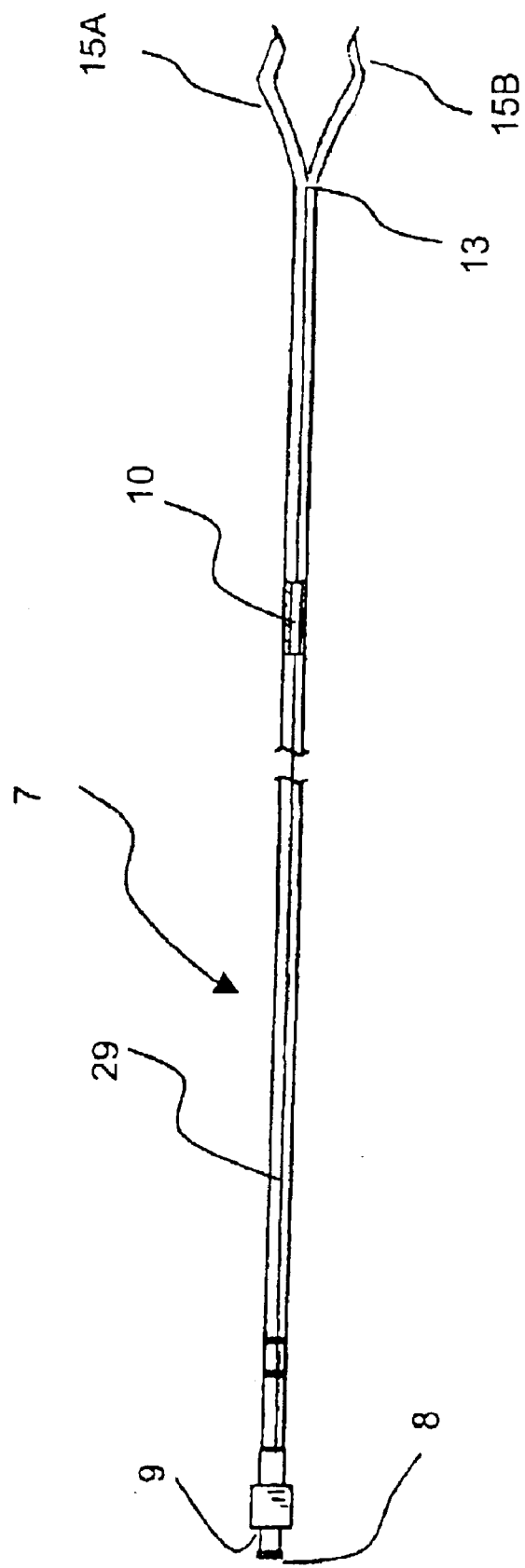
FIG. 7 is a schematic diagram of a leaflet fastening applicator within the guide catheter according to one embodiment of the present invention.

FIG. 7 shows a schematic of a leaflet fastening applicator 7, which may contain a locking port 8 on the proximal end 9 and splits 15A, 15B in the applicator lumen 10 on the applicator distal end 13. The splits 15A, 15B can be configured in different shape, size and functional structures adapted for gripping, securing, fastening and/or coupling two pieces of tissue together. The proximal end 9 can be attached to a vacuum source for the applicator 7 to capture and secure the leaflets by way of vacuum. If the leaflets are to be secured by way of small hooks, individual cables attached to respective hooks are installed in the lumens of the leaflet holders. In another embodiment with energy transmission, the energy transmission route, such as electrical conductors 29, may be provided within the lumen 10 of the applicator 7. One end of the electrical conductor 29 is usually connected to an external energy generator or source.

Figure 8:
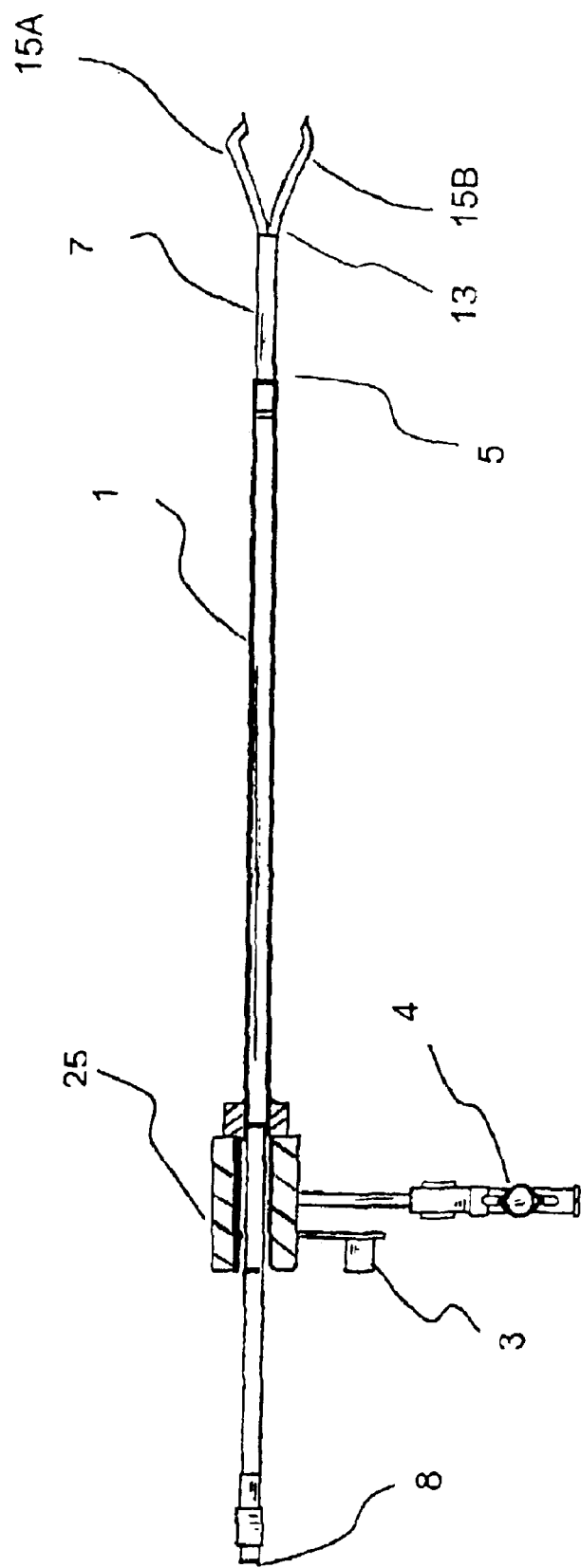
FIG. 8 is a schematic diagram of the leaflet fastening applicator inserted inside the guide catheter as the device system of the present invention.

FIG. 8 depicts the guide catheter in place, with the leaflet fastening applicator 7 contained within the guide catheter 11, wherein the splits 15A, 15B of the leaflet fastening applicator 7 extend out the distal end 5 of the guide catheter 11, such as these two splits may appear when attempting to capture and secure the leaflet(s) or other tissue. In one embodiment, the splits 15A, 15B may comprise a suction arrangement or other means for capturing the flexible leaflet and contain at their end portion a pair of grasping-electrodes for applying radiofrequency energy. The suction arrangement of the splits 15A, 15B may be accomplished by configuring the splits with an inner lumen connecting with an external suction source. In another embodiment, at least one of the splits 15A, 15B may contain at its end portion an ultrasound transducer, an optic fiber for laser or infrared transmission, or an element for electromagnetic energy transmission.

Figure 9:
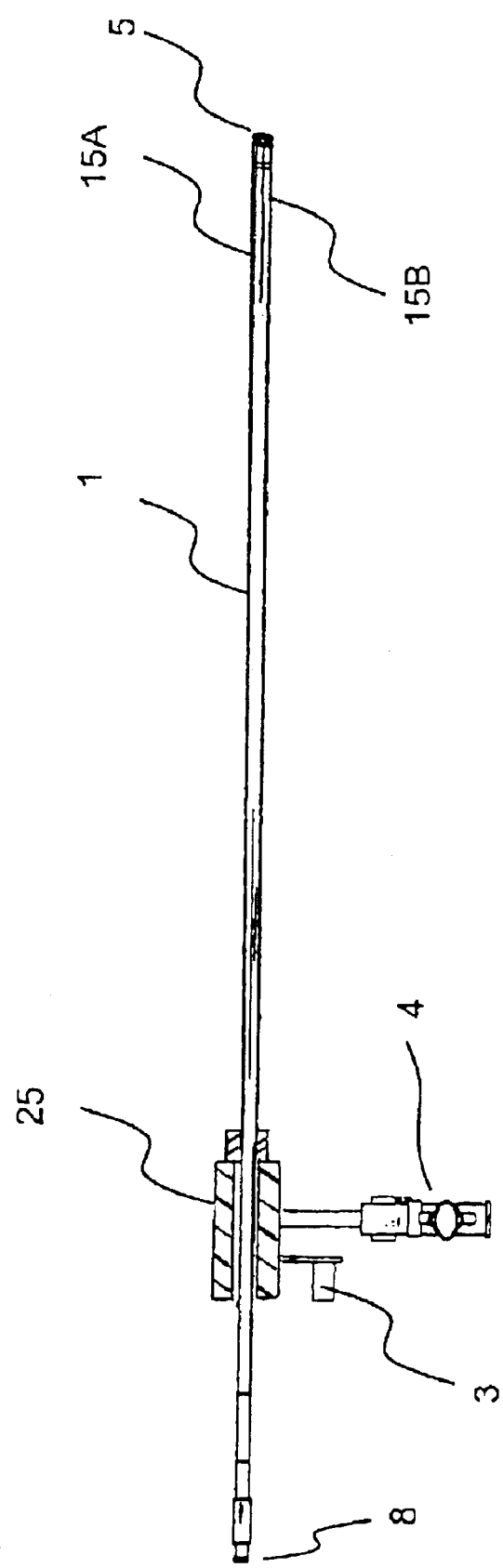
FIG. 9 is a schematic diagram of the leaflet fastening applicator retracted back inside the guide catheter as the device system of the present invention.

FIG. 9 depicts the guide catheter in place, with the leaflet fastening applicator 7 retracted within the guide catheter 11 and the ends of the leaflet fastening applicator 7 drawn slightly into the lumen 2 of the guide catheter 11.

Figure 10:
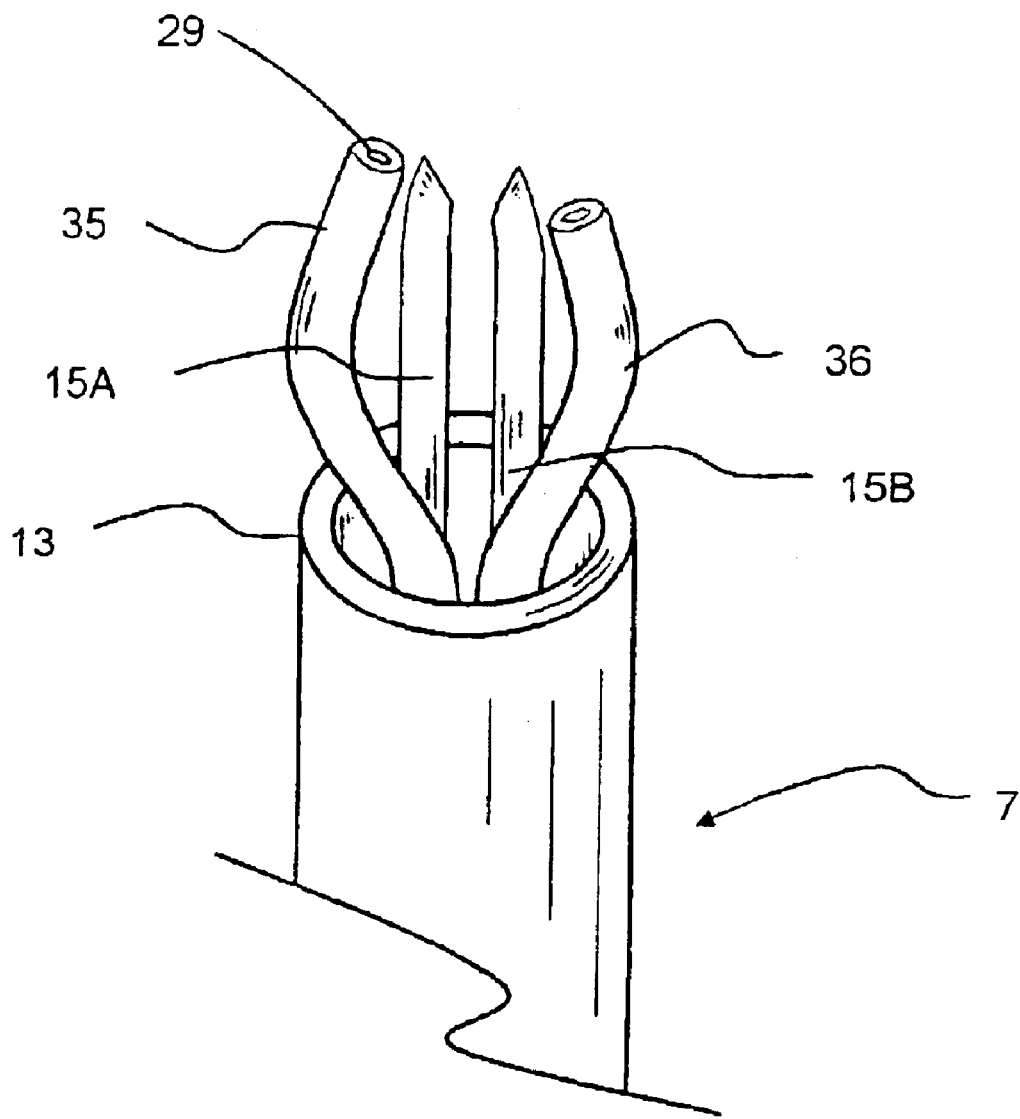
FIG. 10 is an enlarged schematic diagram of the distal end of a preferred embodiment of the leaflet fastening applicator.
Figure 11:
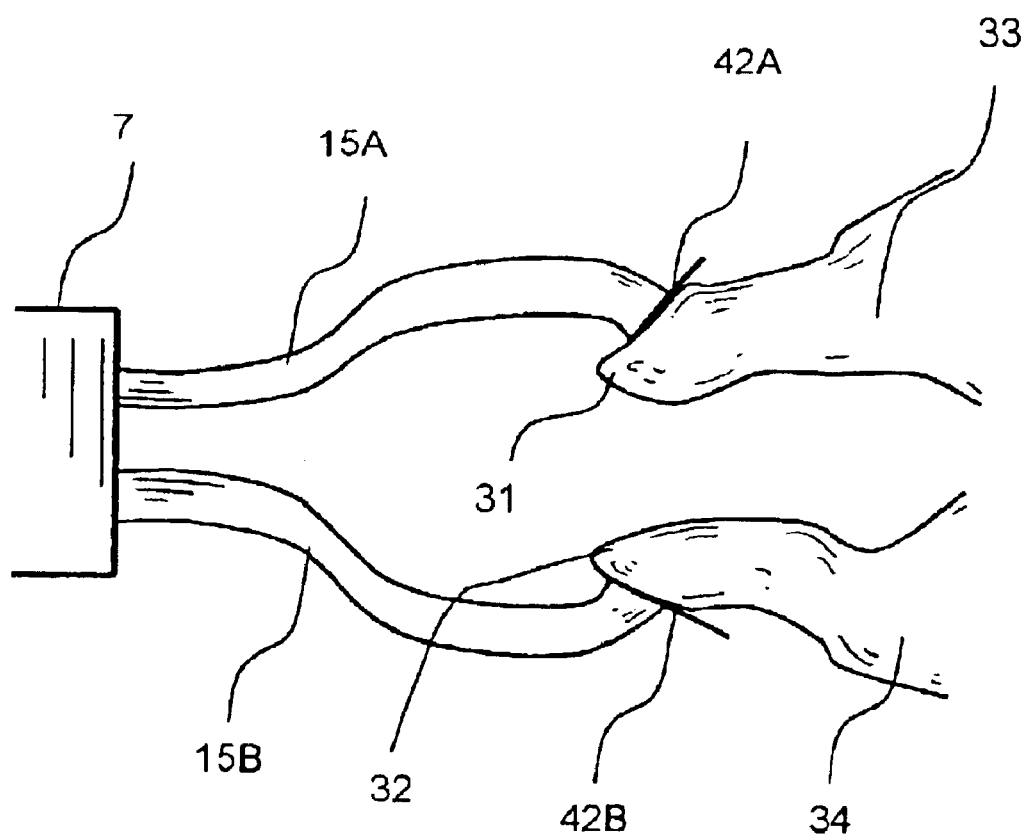
FIG. 11 is a schematic illustration of the leaflet fastening applicator with gradping-electrodes grasping two valve leaflets.
Figure 12:
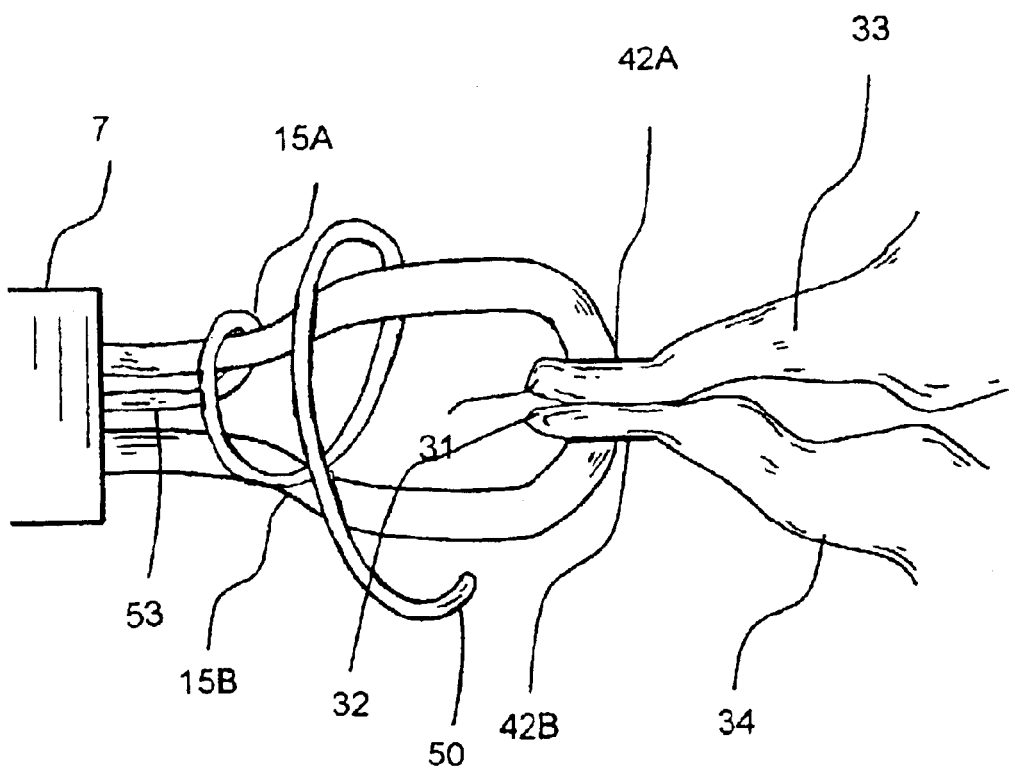
FIG. 12 is a schematic illustration of the leaflet fastening applicator with grasping-electrodes grasping and holding the two valve leaflets together.

In one embodiment, a device system of the present invention as shown in FIG. 10 comprises a guide catheter and a leaflet fastening applicator 7. As illustrated in FIGS. 8 and 9, the guide catheter has suitable dimensions for deployment and insertion into a human heart in a vicinity of a heart valve, wherein the leaflet fastening applicator 7 has a size allowing insertion through the guide catheter 11 and is capable of holding portions of opposing heart valve leaflets (as illustrated in FIG. 11 and FIG. 12). A typical guide catheter may range from about 1 mm in diameter to about 15 mm or larger in diameter. And the guide catheter can be made of any convenient biocompatible material, such as plastic or the like.

As shown in FIG. 10, the device system may further comprise at least a gripper 35 or 36 inside the applicator 7, the gripper having a suitable opening 29 for applying suction to one of the heart valve leaflets or tissue.

As shown in FIGS. 11 and 12, the fastening applicator 7 may optionally comprise a pair of grasping-electrodes 42A, 42B that is mounted at the distal end of the splits 15A, 15B, wherein the grasping-electrodes are configured and adapted for holding and engaging the portions 31, 32 of opposing heart valve leaflets 33, 34 together and for applying radiofrequency energy or other suitable energy to fasten the portions 31, 32. The radiofrequency energy may be introduced from an external radiofrequency source and passes from the first grasping-electrode 15A through the portions of opposing heart valve leaflets 31, 32 to the second grasping-electrode 15B. The device is equally applicable to a venous valve. The bi-polar radiofrequency arrangement and principles for tissue welding or fastening are well known to an ordinary artisan who is skilled in the art.

For illustration purposes as shown in FIG. 12, it is provided a non-ablative energy means 50 for shrinking at least a portion of the valvular annulus 52. One example of the non-ablative energy means is a deployable spiral wire electrode at a distal end of an elongate shaft 53 adapted to contact the tissue of the valvular annulus to be treated and to apply high frequency energy to the tissue for therapeutic purposes. A deployable spiral wire electrode is well known to one ordinary skill in the art and is disclosed in U.S. Pat. No. 6,267,781 that is co-invented by one of the current applicants. The energy for treating annulus tissue may be selected from a group consisting of radiofrequency, ultrasound, laser, microwave, electromagnetic, and combination thereof. The term "non-ablative" energy is herein intended to mean the energy sufficiently suitable to shrink or tighten collagen or tissue; however, the non-ablative energy is below the tissue ablation threshold that causes tissue injury or necrosis irreversibly.

For illustration purposes, another example of non-ablative energy means is a rotational electrode with sweeping force at the distal section of the tubular element to effect the heat treatment and the rotational sweeping massage therapy for target annulus tissues. A rotatable electrode is well known to one ordinary skill in the art and is disclosed in U.S. Pat. No. 6,283,962 that is co-invented by one of the current applicants. The energy for treating annulus tissue may be selected from a group consisting of radiofrequency, ultrasound, laser, microwave, electromagnetic, and combination thereof.

For illustration purposes, still another example of non-ablative energy means is an apparatus capable of sandwiching and compressing the annulus and applying heat sufficient to shrink or tighten tissue surrounding the annulus tissue. A sandwichable electrode is well known to one ordinary skill in the art and is disclosed in U.S. Pat. No. 6,485,489 that is co-invented by two of the current applicants. The energy for treating annulus tissue may be selected from a group consisting of radiofrequency, ultrasound, laser, microwave, electromagnetic, and combination thereof.

Figure 13:
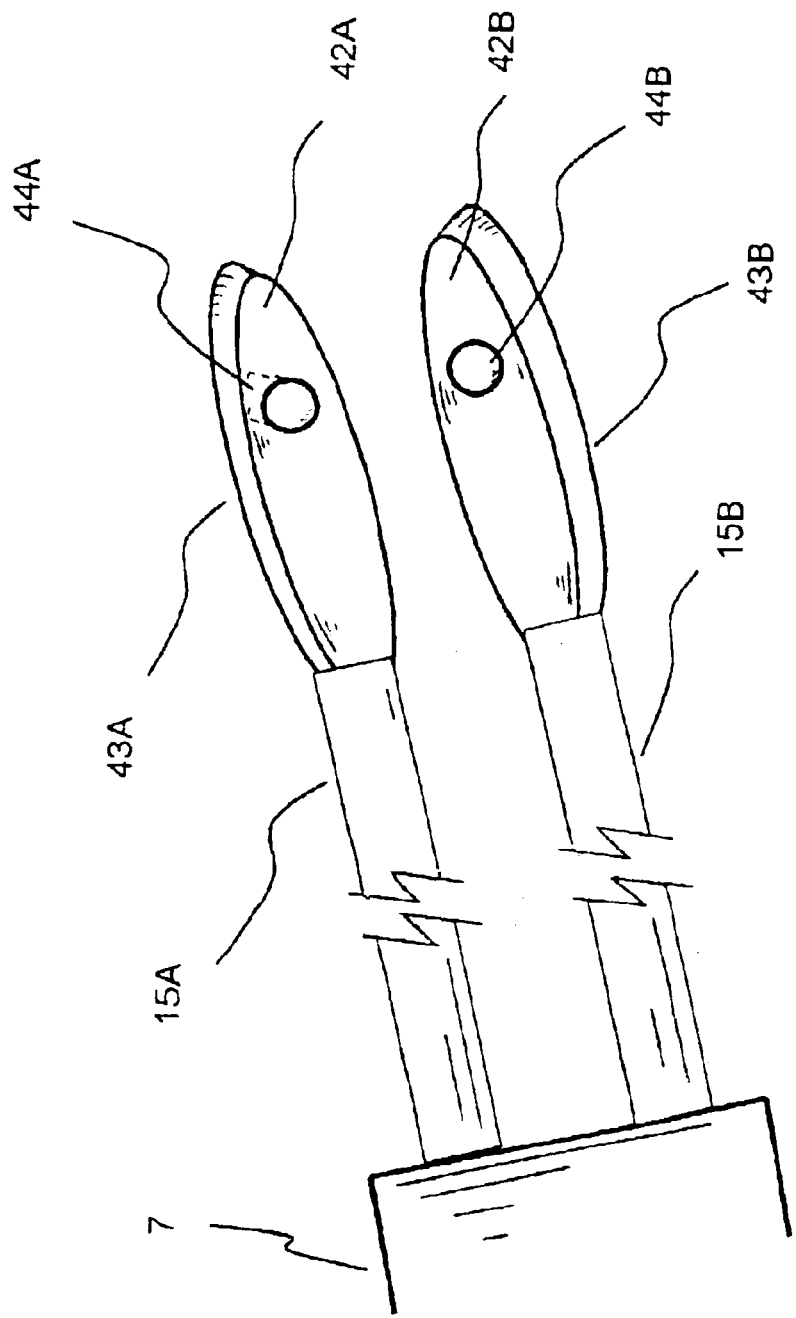
FIG. 13 is a detailed perspective view of the grasping-electrodes with a first hole on the first grasping-electrode and a second hole that is aligned with the first hole.

As shown in FIG. 13, the first grasping-electrode 42A of the present invention may comprise a first hole 44A and the second grasping-electrode 42B comprises a second hole 44B that is aligned with the first hole 44A, the first and second holes being adapted suitable for inserting a suture, a staple, a hook or other attachment device to fasten the portions of the opposing heart valve leaflets. The aligned holes are particularly suitable for any conventional types of tissue coupling and fastening. The exterior surfaces 43A, 43B of the non-contacting sides of the grasping-electrodes 42A, 42B in FIGS. 13 to 15 can be smooth surfaces or other appropriate arrangement.

Figure 14:
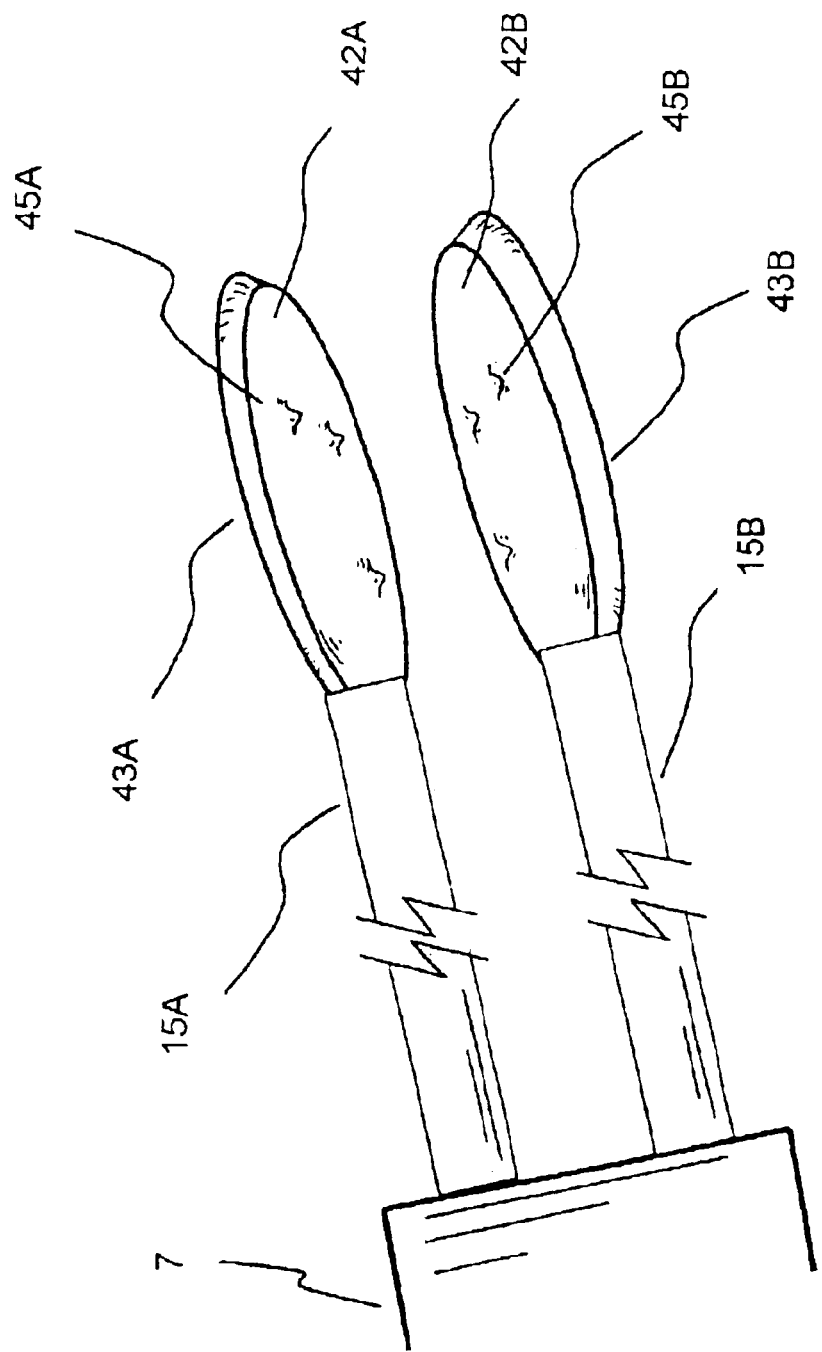
FIG. 14 is a detailed perspective view of the grasping-electrodes with a plurality of spikes on a first grasping-electrode and a plurality of recesses on a second grasping-electrode configured to engage the spikes of the first grasping-electrode.

In another embodiment as shown in FIG. 14, a first grasping-electrode 42A of the grasping-electrodes arrangement may comprise a plurality of spikes 45A and a second grasping-electrode 42B of the grasping-electrodes comprises a plurality of recesses 45B configured to engage the spikes 45A of the first grasping-electrode 42A, wherein the spikes' sharp ends of the first grasping-electrode pushes the body tissue into the recesses of the second grasping-electrode with enhanced grasping capability.

Scott et al. in U.S. Pat. No. 5,527,313 discloses a device wherein a first grasping-electrode has a plurality of spikes and a second grasping-electrode has a plurality of spikes configured to engage the spikes of the first grasping-electrode. Both jaws have a plurality of spikes and valleys in between the spikes. U.S. Pat. No. 5,527,313 further shows the two grasping-electrodes at an open position with the spikes' sharp ends of the first jaw facing the spikes' sharp ends of the second jaw whereas the two grasping electrodes at a closed position with the spikes' sharp ends of the first jaw falling into the valleys of the opposite spikes of the second jaw in a manner that does not push the body tissue into the recesses of the second grasping-electrode. And therefore, the prior art device does not have enhanced grasping capability.

Figure 15:
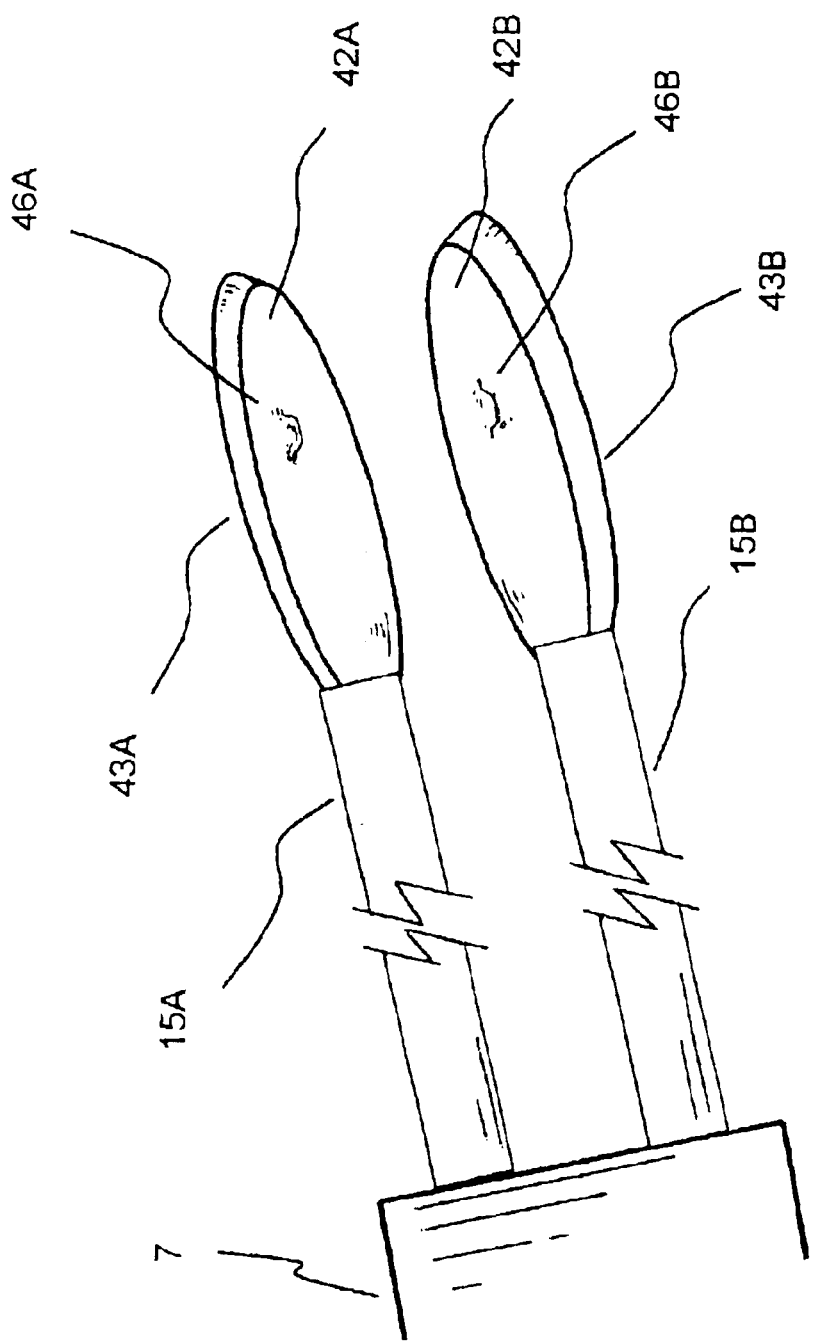
FIG. 15 is a detailed perspective view of the grasping-electrodes with one clip button set having a notch on the first grasping-electrode and a lip on the second grasping-electrode.

In a further embodiment of FIG. 15, the pair of grasping-electrodes of the device system is configured to comprise at least one clip button set, wherein each of the at least one clip button set has a notch 46A on the first grasping-electrode 42A and a lip 46B on the second grasping-electrode 42B in which the notch 46A engages the lip 46B when the grasping-electrodes 42A, 42B are held close to each other for tissue fastening purposes.

Figure 16:
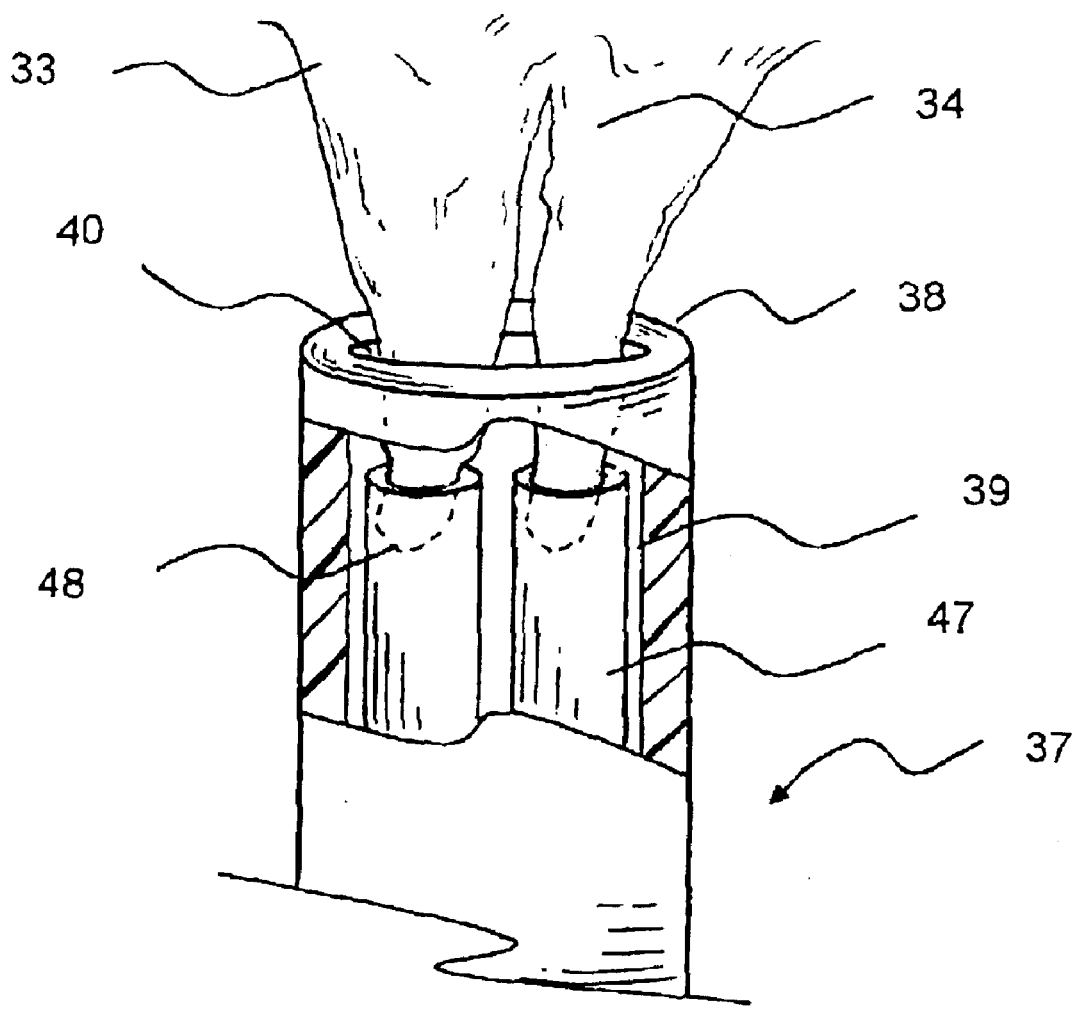
FIG. 16 is an enlarged view of one embodiment of the invention, wherein the guide catheter is configured such that the distal opening provides access for securing a pair of the valve leaflets adapted for fastening the edges of leaflets with an energy welding method or a mechanical coupling method.

In a preferred embodiment as shown in FIG. 16, the device system of the present invention may further comprise a tubular gripper 37 having a distal end 38 and a lumen 39, the tubular gripper 37 having a suitable opening 40 at its distal end 38 for applying suction to grip at least two of the target heart valve leaflets 33, 34 to enter the lumen 39 adapted for fastening the portions of opposing heart valve leaflets together using a mechanical fastening method or energy fastening method. In an alternate embodiment, a plurality of suction tubular elements 47, 48 is positioned within the lumen 39 of the tubular gripper 37. The adjacent leaflet edges are held in place within elements 47, 48 with constant vacuum. In this position, the cardiologist can evaluate the effects of attaching the leaflets, by examining the flow of contrast medium or examining flow with ultrasound, during the beating of the heart and the flow and ebb of blood at the valve. An ultrasonic imaging system may be incorporated during the procedure to assist the cardiologist. The fastening means may comprise energy welding or mechanical fastening.

Some aspects of the invention relate to a device system for treating a valvular annulus comprising a guide catheter and a leaflet fastening applicator, the guide catheter having suitable dimensions for deployment and insertion into a human heart in a vicinity of a heart valve and comprising a non-ablative energy means for shrinking at least a portion of the valvular annulus, the leaflet fastening applicator having a size allowing insertion through the guide catheter and being capable of holding portions of opposing heart valve leaflets, wherein the fastening applicator comprises a pair of grasping-electrodes adapted for holding and engaging the portions of opposing heart valve leaflets together and for applying radiofrequency energy to fasten the portions, wherein a first of the grasping-electrodes comprises a plurality of spikes and a second of the grasping-electrodes comprises a plurality of recesses configured to receivably match and engage the spikes of the first grasping-electrode, wherein the catheter comprises at least a gripper inside the catheter, the gripper having a suitable opening sized and configured for applying vacuum suction to releasably grip one of the heart valve leaflets. The non-ablative energy means may be selected from a group consisting of radiofrequency energy, ultrasound energy, laser energy, electromagnetic energy, microwave energy and the like.

One mode of performing the method of the present invention is to have a catheter introduced via aortic valve or more commonly across atrial septum as in balloon valvuloplasty of the mitral valve. After entrapment of leaflets, a stapling device is pushed to site where anterior and posterior leaflets approximate each other. The staple, suture or other attachment device is guided to approximate leaflets and pulled back to ensure both leaflets are caught and then released. This stapling step may optionally be added to the energy-assisted leaflets welding/fastening disclosure of the present invention with at least one energy source, wherein the energy source is selected from a group consisting of radiofrequency energy, ultrasound energy, laser energy, electromagnetic energy, cryogenic energy, microwave energy and the like.

In some preferred aspects, it is provided a method for treating a valvular annulus, comprising: (a) fastening portions of two opposite leaflets; and (b) applying energy to the valvular annulus adapted for shrinking at least a portion of the annulus tissue. In one embodiment, the steps of fastening portions of two opposite leaflets and applying energy are carried out percutaneously. In another embodiment, the steps of fastening portions of two opposite leaflets and applying energy are carried out through an open chest procedure. In still another embodiment, the energy for shrinking at least a portion of the annulus tissue is selected from a group consisting of radiofrequency energy, ultrasound energy, electromagnetic energy, microwave energy, laser energy, and cryogenic energy.

Although the explanations and illustration herein have used the mitral valve as an example, the devices in either embodiment can be used on mitral, tricuspid, aortic or pulmonary valves as indicated for the improvement in leaflet coaptation and valve competence, during normal heart/blood cycling, without the need for costly, risky and painful open-heart surgery and cardiopulmonary bypass. This invention is not a complete replacement for the repair offered by cardiothoracic surgeons in repair of these heart valves. Practically, there are certain cases, which can be aided only through open-heart procedures. However, this invention should serve a significant segment of the population, who will be assisted with the type of repairs offered by these methods and devices.

U.S. Pat. No. 6,267,781, co-invented by one of the current applicants, teaches a non-ablative energy treating device for treating valvular annulus or valvular organ structure of a patient, comprising a flexible elongate tubular shaft having a deployable spiral wire electrode at its distal end adapted to contact/penetrate the tissue to be treated and to apply high frequency energy to the tissue for therapeutic purposes. U.S. Pat. No. 6,283,962, co-invented by one of the current applicants, discloses a medical energy device system for treating valvular annulus wherein an elongate tubular element comprises an electrode disposed at its distal section that is extendible from an opening at one side of the tubular element, the energy generator, and means for generating rotational sweeping force at the distal section of the tubular element to effect the heat treatment and the rotational sweeping massage therapy for target tissues. Both patents, entire contents of which are incorporated herein by reference, teach the local tissue shrinkage, not for simultaneously fastening portions of two opposite valve leaflets together to enhance annulus repairing and function.

U.S. Pat. No. 6,306,133, co-invented by one applicant of the present invention, entire contents of which are incorporated herein by reference, discloses a non-ablative energy catheter system and methods for repairing an annular organ structure comprising high frequency non-ablative energy for the purposes of tightening and stabilizing a tissue. A catheter suitable for high frequency energy delivery comprises a flexible tissue-contactor means located at the distal tip section of a catheter shaft for contacting an inner wall of the annular organ structure, and a needle electrode means located at or within the flexible tissue-contactor means for penetrating into the tissue, wherein the needle electrode means is deployable out of the tissue-contactor means in a manner essentially perpendicular to a longitudinal axis of the catheter shaft.

U.S. Pat. No. 6,485,489, co-invented by two applicants of the present invention, entire contents of which are incorporated herein by reference, discloses a catheter system and methods for repairing a valvular annulus of a patient comprising sandwiching and compressing the annulus and applying heat sufficient to shrink or tighten tissue surrounding the annulus defect. Some aspects of the invention relate to simultaneously fastening the leaflets together and applying energy effective to shrink or tighten annulus tissue for annulus repairing.

From the foregoing description, it should now be appreciated that an energy-assisted tissue fastening approach percutaneously for valve leaflets fastening has been disclosed. While the invention has been described with reference to a specific embodiment, the description is illustrative of the invention and is not to be construed as limiting the invention. Various modifications and applications may occur to those who are skilled in the art, without departing from the true spirit and scope of the invention, as described by the appended claims.

What is claimed is:

1. A device system for treating a valvular annulus comprising a guide catheter and a leaflet fastening applicator, said guide catheter having suitable dimensions for deployment and insertion into a human heart in a vicinity of a heart valve and comprising a non-ablative energy means for shrinking at least a portion of the valvular annulus, said leaflet fastening applicator having a size allowing insertion through said guide catheter and being capable of holding portions of opposing heart valve leaflets, wherein said fastening applicator comprises a pair of grasping-electrodes adapted for holding and engaging said portions of opposing heart valve leaflets together and for applying radiofrequency energy to fasten said portions, wherein a first of said grasping-electrodes comprises a plurality of spikes and a second of said grasping-electrodes comprises a plurality of recesses configured to receivably match and engage the spikes of said first grasping-electrode, wherein said catheter comprises at least a gripper inside the catheter, said gripper having a suitable opening sized and configured for applying vacuum suction to releasably grip one of said heart valve leaflets.

2. The device system of claim 1, wherein the non-ablative energy means comprises radiofrequency energy.

3. The device system of claim 1, wherein the non-ablative energy means comprises ultrasound energy.

4. The device system of claim 1, wherein the non-ablative energy means comprises laser energy.

5. The device system of claim 1, wherein the non-ablative energy means comprises electromagnetic energy.

6. The device system of claim 1, wherein the non-ablative energy means comprises microwave energy.

7. The device system of claim 1, wherein the guide catheter further comprises a lumen for solution injection.

8. The device system of claim 7, wherein the solution for injection is selected from a group consisting of heparin, aspirin, saline, antibiotic solution, anti-inflammatory solution, and anti-septic solution.

* * * * *